US011099167B2

(12) United States Patent
Dubs

(10) Patent No.: US 11,099,167 B2
(45) Date of Patent: Aug. 24, 2021

(54) METHODS TO DETERMINE PRESSURE DISTRIBUTION ALONG A DOWNHOLE FORMATION AND TO DETERMINE A RECIPE FOR MATERIALS USED IN A WELLBORE

(71) Applicant: Halliburton Energy Services, Inc., Houston, TX (US)

(72) Inventor: Liam Dubs, Forth Worth, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 151 days.

(21) Appl. No.: 16/579,557

(22) Filed: Sep. 23, 2019

(65) Prior Publication Data

US 2021/0088498 A1 Mar. 25, 2021

(51) Int. Cl.
*G01N 33/24* (2006.01)
*E21B 49/02* (2006.01)
*G01N 33/38* (2006.01)

(52) U.S. Cl.
CPC ............ *G01N 33/24* (2013.01); *E21B 49/02* (2013.01); *G01N 33/383* (2013.01)

(58) Field of Classification Search
CPC .... G01N 1/28; G01N 3/12; G01N 33/24; G01N 33/383; G01N 2203/0232; E21B 49/00; E21B 49/02; E21B 49/003
See application file for complete search history.

(56) References Cited

U.S. PATENT DOCUMENTS

| 6,548,164 | B1 | 4/2003 | Bacon, Jr. |
| 7,121,155 | B2 | 10/2006 | Johansson et al. |
| 10,067,011 | B2 | 9/2018 | King et al. |
| 2005/0158540 | A1 | 7/2005 | Sakai |

*Primary Examiner* — Benjamin R Schmitt
(74) *Attorney, Agent, or Firm* — McGuireWoods LLP

(57) ABSTRACT

Methods to determine pressure distribution along a downhole formation and methods to determine a recipe for materials used in a wellbore are disclosed. A method to determine pressure distribution along a downhole formation includes overlaying a pressure film on a formation sample of a downhole formation. The method also includes inserting cement, the pressure film and the formation sample in a pressure vessel. The method further includes utilizing the pressure vessel to perform one or more tests of the formation sample. After performing the one or more tests, the method further includes analyzing the pressure film to determine a pressure distribution along the formation sample.

20 Claims, 4 Drawing Sheets

METHODS TO DETERMINE PRESSURE DISTRIBUTION ALONG A DOWNHOLE FORMATION AND TO DETERMINE A RECIPE FOR MATERIALS USED IN A WELLBORE

BACKGROUND

The present disclosure relates generally to methods to determine pressure distribution along a downhole formation and methods to determine a recipe for materials used in a wellbore.

Samples of downhole formations are sometimes obtained and analyzed to determine one or more properties of the formation, plan for drilling, cementing and other well operations, and to determine specifications of tools and recipes of materials used in subsequent well operations. More particularly, a formation sample is sometimes inserted into a pressure vessel together with samples of cement and other materials that are poured and cured around the formation sample, and one or more types of formation testing operations are performed on the formation sample or other materials deposited around the formation sample. However, it is difficult to determine pressure exerted on the formation sample as well as the distribution of pressure at different locations of interest of the formation sample while the formation sample is deposited in the pressure vessel.

BRIEF DESCRIPTION OF THE DRAWINGS

The following figures are included to illustrate certain aspects of the present disclosure and should not be viewed as exclusive embodiments. The subject matter disclosed is capable of considerable modifications, alterations, combinations, and equivalents in form and function, without departing from the scope of this disclosure.

Figure 1:
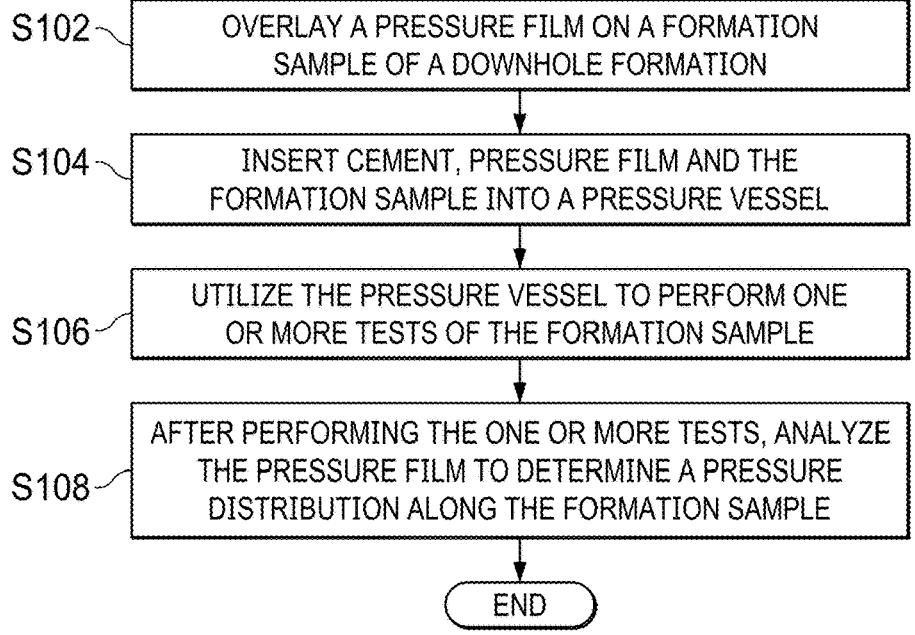
FIG. 1 illustrates a flowchart of a process to determine pressure distribution along a downhole formation.

The illustrated figures are only exemplary and are not intended to assert or imply any limitation with regard to the environment, architecture, design, or process in which different embodiments may be implemented.

DETAILED DESCRIPTION OF ILLUSTRATIVE EMBODIMENTS

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments is defined only by the appended claims.

The present disclosure relates to methods to determine pressure distribution along a downhole formation and methods to determine a recipe for materials used in a wellbore. A formation sample is extracted from a downhole or aboveground location. A pressure film is overlaid on the formation sample of a downhole formation. As referred to herein, a pressure film is any film or material that is sensitive to pressure applied to or towards the film. In some embodiments, cement to be used during a cementing operation is poured into a casing cup and is kept at room temperature or in conditions similar to downhole conditions of an area downhole where the cementing operation will be performed. In some embodiments, materials that form an annulus of a wellbore are also poured into a casing cup and are kept at room temperature or in conditions similar to downhole conditions of an area downhole where the annulus is formed. As used herein, an annulus refers to the materials used to isolate the casing from the formation. In some embodiments, the cement is first cured, after which the cured cement, pressure film, and formation sample are inserted into a pressure vessel.

In some embodiments, the cement, pressure film, and formation sample are inserted into the pressure vessel and the cement is cured in-situ. As referred to herein, a pressure vessel includes any vessel or container operable to store a formation sample, where testing operations of the formation sample are performed within the vessel. The pressure vessel is utilized to perform tests on the formation sample. In one or more of such embodiments, a chamber of the pressure vessel that contains the formation sample is pressurized to match downhole conditions. After testing of the formation sample is complete, the pressure film is removed from the pressure vessel and is analyzed to determine the pressure distribution of the formation sample. In some embodiments, where the pressure film is placed in between the formation sample and the cement, the pressure film is analyzed to determine the pressure distribution between the formation sample and the cement. In some embodiments, after the pressure film is removed, the formation sample is reassembled and additional testing, such as API RP19B Section 2 and API RP19B Section 4 tests, are performed on the formation sample. In some embodiments, where the pressure film is placed in between the formation sample and the annulus, the pressure film is analyzed to determine the pressure distribution between the formation sample and the annulus.

In some embodiments, the pressure film has a clear, transparent, translucent, white, or a different initial color before any pressure is applied to the pressure film. Moreover, pressure applied to the pressure film results in coloring of the pressure film, where the initial color is changed to a different color. For example, where the pressure film initially has a white color, applying pressure on an area of the pressure film results in the color of the area to change from white to red or another color. Further, different amounts of pressure applied to certain areas of the pressure film result in different colors applied to the pressure film. In one or more of such embodiments, the amount of pressure applied to an area of the pressure film corresponds to a color within a range of colors displayed on the pressure film. Continuing with the foregoing example where the initial color of the pressure film is white, applying a gradient of pressure on different areas of the pressure film results in the color of the respective areas of the pressure film to change from white to a gradient of red colors, where the darkness of the red color corresponds to the amount of pressure applied to the corresponding area of the pressure film. In one or more of such embodiments, each color corresponds to a specific amount of pressure, or a range of pressures. In one or more of such embodiments, the coloring of the pressure film due to pressure applied to the formation sample during testing is analyzed to determine the amount of pressure applied to a corresponding location of the formation sample. For example, zero pressure corresponds to white color, 1-10 psi corresponds to a first shade of red color, 11-20 psi corresponds to a second shade of red color, 31-30 psi corresponds to a third shade of red color, and every 10 psi above 30 psi corresponds to a different shade of red or another unique color within a range of colors.

In some embodiments, two or more pressure films are overlaid on the formation sample. In one or more of such embodiments, each pressure film is sensitive to a different range of pressures and is used to measure a different range of pressures applied to the formation sample, where different amounts of pressure applied to different areas of the respective pressure film results in different color changes at the respective areas of the pressure film. For example, where a first pressure film that is sensitive to pressure between 0-1,000 psi and a second pressure film that is sensitive to pressure between 1,001 psi and 2,000 psi are overlaid on the formation sample, applying varying amounts of pressure between 200-1,000 psi on a first set of areas of interest results in different coloring of the first pressure film, such as varying shades of red (or a different color gradient), where each shade of red corresponds to a particular pressure or range of pressures applied to a corresponding location of the formation sample. Further, applying varying amounts of pressure between 1,200-1,800 psi on a second set of areas of interest results in different coloring of the second pressure film, such as varying shades of green (or a different color gradient), where each shade of green corresponds to a particular pressure or range of pressures applied to a corresponding location of the formation sample.

In some embodiments, applying a pressure that is not within a range of pressures that a pressure film is sensitive to does not result in a change of color of the pressure film. Continuing with the foregoing example, a pressure under 1,000 psi does not result in a change of color of the second pressure film. Alternatively, applying a pressure that is not within a range of pressures that a pressure film is sensitive to results in the original color of the pressure film to change to a color that indicates the applied pressure is not within the range of pressures the pressure film is sensitive to. Continuing with the foregoing example, a pressure under 1,000 psi results in a change of color of the second pressure film to blue or another color that indicates the applied pressure is not within the range of pressures the second pressure film is sensitive to.

In some embodiments, different pressure films sensitive to overlapping ranges of pressure are overlaid on the formation sample. For example, a first pressure film sensitive to pressure between 0-2,000 psi and a second pressure film sensitive to pressure between 1,000-10,000 psi are overlaid on the formation sample. In one or more embodiments, the pressure films are not only used to measure pressure within both ranges of pressure, but are also used to confirm the accuracy of the measurements of pressures within an overlapping range of pressures.

In some embodiments, an operator analyzes the colors present on the pressure films, and matches the colors to different amounts of pressure exerted on corresponding areas of interest of the formation sample and pressure differential across the formation sample. In some embodiments, the processes of analyzing the colors present on the pressure films and determining the amount of pressure exerted on corresponding areas of interest of the formation sample are performed dynamically by an electronic device operable to dynamically perform the processes.

The present disclosure also relates to methods to determine recipes for materials used in a wellbore, such as cement used during cement operations, and materials used to form an annulus. For example, the pressure distribution between the formation and the cement is analyzed and used to adjust cement recipes used to manufacture cement that shrinks less during a curing process, shrinks more during the curing process, or satisfies other desirable specifications. Similarly, the pressure distribution between the formation and the annulus is analyzed and used to adjust recipes used to manufacture an annulus that shrinks less during a curing process, shrinks more during the curing process, or satisfies other desirable specifications. Certain steps of the process to determine recipes for materials used in the wellbore including overlaying a pressure film on a formation sample of a downhole formation, inserting cement, pressure film and the formation sample in a pressure vessel, utilizing the pressure vessel to perform one or more tests of the formation sample, and analyzing the pressure film to determine a pressure distribution along the formation sample, are similar to processes to determine pressure distribution of a downhole formation and are described herein. Further, a recipe for manufacturing cement or another material deployed in the wellbore is then determined based on the pressure distribution along the formation sample. For example, where the pressure film is placed in between the formation sample and the cement, the pressure distribution between the formation sample and the cement is analyzed to determine the material properties of the cement and to determine whether the cement is overloaded, underloaded, or is neither overloaded nor underloaded during perforation. The recipe for the cement is then fine-tuned if the cement is overloaded or underloaded to prevent either adverse condition.

Similarly, where the pressure film is placed in between the formation sample and an annulus, the pressure distribution between the formation sample and the annulus is analyzed to determine the material properties of the annulus and to determine whether the annulus is overloaded, underloaded, or is neither overloaded nor underloaded during perforation. The recipe for the annulus is then fine-tuned if the annulus is overloaded or underloaded to prevent either adverse condition. Additional descriptions and illustrations of the foregoing processes are provided in the paragraphs below.

Turning now to the figures, FIG. 1 is a flowchart of a process 100 to determine pressure distribution along a downhole formation. Although the operations in process 100 are shown in a particular sequence, certain operations may be performed in different sequences or at the same time where feasible.

At block S102, a pressure film is overlaid on a formation sample of a downhole formation. At block S104, cement, pressure film, and the formation sample are inserted into a pressure vessel. In some embodiments, cement is poured into a pressure cup and is cured before the cement is inserted into the pressure vessel. In such embodiments, the pressure film is placed in between the formation sample and the cement. Similarly, in some embodiments, materials used to construct an annulus are also poured into a pressure cup, the annulus is cured before the annulus is inserted into the pressure vessel. In such embodiments, the pressure film is placed in between the formation sample and the annulus. At block S106, the pressure vessel is utilized to perform one or more tests of the formation sample. In one or more of such embodiments, the pressure vessel is pressurized to match downhole conditions. In some embodiments, testing of the penetration of the formation sample is conducted while the formation sample is in the pressure vessel.

At block S108, and after performing the one or more tests, the pressure film is analyzed to determine a pressure distribution along the formation sample. In some embodiments, the pressure film is analyzed to determine the pressure distribution along surfaces of the formation sample and the cement. In some embodiments, the color of the pressure film at a location of interest changes in response to pressure applied to the pressure film at the location of interest. In one or more of such embodiments, the color changes from an initial color (e.g., clear, white, or another color) to a different color within a range of colors (e.g., a range of shades of red or a different range within the color spectrum) that illustrate the pressure distribution of the formation sample, where each color corresponds to a different amount of pressure within a range of pressures applied to a corresponding location of interest of the formation sample. For example, where the color of the pressure film at a location of interest changes to dark red, and where dark red corresponds to 1,500 psi, then the pressure applied to the corresponding location of the formation sample (e.g., the location directly under the location of interest of the pressure film) is 1,500 psi. In some embodiments, different color gradients represent different ranges of pressure applied to a location of interest. For example, a color within a range of red colors at the location of interest indicates the pressure at the corresponding location of interest of the formation sample is between 1,400-1,600 psi, whereas a color within a range of green colors at a second location of interest indicates the pressure at the second corresponding location of interest of the formation sample is between 2,000-2,500 psi.

In some embodiments, a second pressure film is also overlaid on the formation sample, where the color of the second pressure film at a location of interest changes in response to pressure applied to the pressure film at the location of interest. In one or more of such embodiments, the first pressure film and the second pressure film are sensitive to different ranges of pressure. For example, where a first pressure film that is sensitive to pressure between 0-2,000 psi and a second pressure film that is sensitive to pressure between 1,000-10,000 psi are overlaid on the formation sample, applying varying amounts of pressure between 500-1,500 psi on a first set of areas of interest results in different coloring of the first pressure film, such as varying shades of red (or a different color gradient), where each shade of red corresponds to a particular pressure or range of pressures applied to a corresponding location of the formation sample. Further, applying varying amounts of pressure between 1,200-1,800 psi on a second set of areas of interest results in different coloring of the second pressure film, such as varying shades of green (or a different color gradient), where each shade of green corresponds to a particular pressure or range of pressures applied to a corresponding location of the formation sample. In some embodiments, applying a pressure that is not within a range of pressures that a pressure film is sensitive to does not result in a change of color of the pressure film. For example, the initial color of the second pressure film would not change if 50 psi of pressure is applied to an area of the formation sample under the second pressure film. In some embodiments, the range of the pressures measured by the first and the second pressure films do not overlap to measure a broader range of pressures.

In some embodiments, color change to each area of the pressure film is analyzed to determine the pressure applied to the formation of interest of a corresponding area of the formation sample that lays under the pressure film, and to determine the pressure distribution of the formation sample across areas under the pressure film. In some embodiments, the pressure film is placed between the formation sample and the cement, and the pressure film is analyzed to determine the pressure distribution along the surfaces of the formation sample and the cement. Similarly, in one or more of such embodiments, where the pressure film is placed between the formation sample and the annulus, the pressure film is analyzed to determine the pressure distribution along the surfaces of the formation sample and the annulus.

Figure 2:
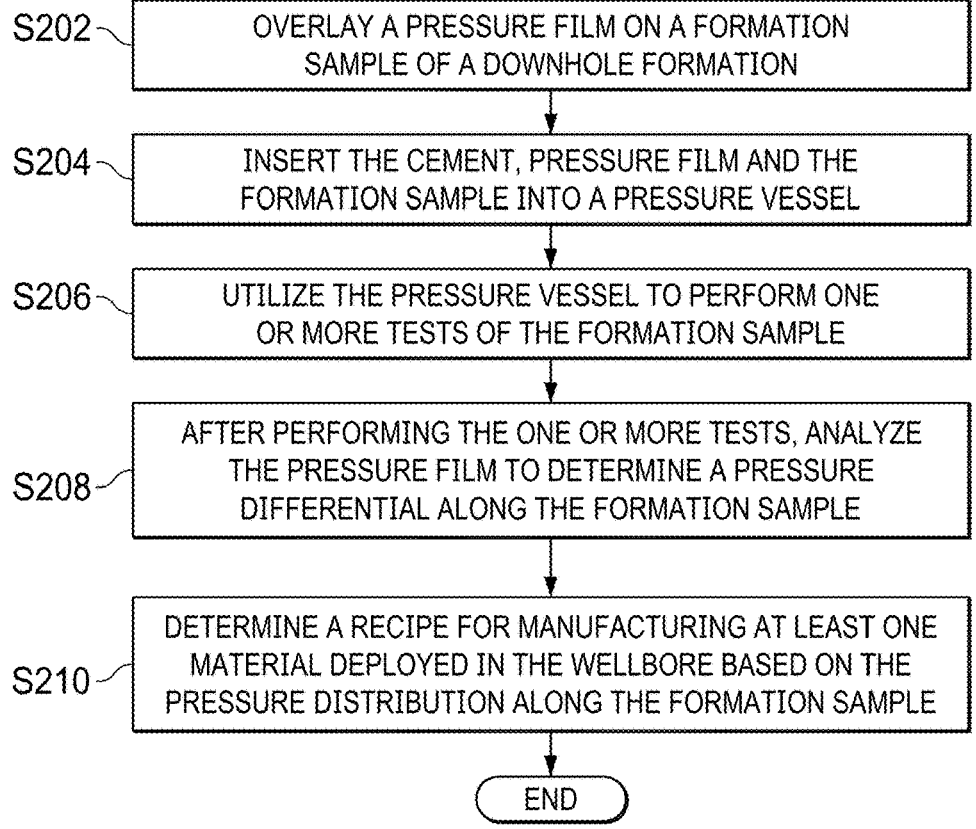
FIG. 2 illustrates a flowchart of a process to determine a recipe for materials used in a wellbore.

FIG. 2 is a flowchart of a process 200 to determine a recipe for materials used in a wellbore. Although the operations in process 200 are shown in a particular sequence, certain operations may be performed in different sequences or at the same time where feasible.

At block S202, a pressure film is overlaid on a formation sample of a downhole formation. At block S204, cement, pressure film, and the formation sample are inserted into a pressure vessel. At block S206, the pressure vessel is utilized to perform one or more tests of the formation sample. At block S208, and after performing the one or more tests, the pressure film is analyzed to determine a pressure distribution along the formation sample. The processes performed at blocks S202, S204, S206, and S208 are similar to the processes performed at blocks S102, S104, S106, and S108, and described in the paragraphs herein.

At block S210, a recipe for manufacturing at least one material deployed in the wellbore is determined based on the pressure distribution along the formation sample. For example, a recipe for cement to be used in the wellbore is determined by placing a pressure film between the formation sample and cement in the pressure vessel, analyzing the pressure film to determine a pressure distribution between the formation sample and the cement, and determining the recipe for the cement based on the pressure distribution between the formation sample and the cement poured over the pressure film. In one or more embodiments, where a desirable pressure distribution is sought, an existing recipe for cement that results in an undesirable pressure distribution (e.g., the pressure distribution is outside of the desired pressure range or distribution range) is modified, new cement formed from a new recipe is poured over the pressure film, and pressure distribution between the formation sample and the new cement is analyzed to determine whether the pressure distribution is within a tolerance of the desired pressure distribution. In some embodiments, the process illustrated in FIG. 2 is repeated until a cement recipe that forms cement having a desired pressure distribution is determined.

Similarly, a recipe for an annulus to be used in the wellbore is determined by placing a pressure film between the formation sample and a sample of the annulus in the pressure vessel, analyzing the pressure film to determine a pressure distribution between the formation sample and the annulus, and determining the recipe for the annulus based on the pressure distribution between the formation sample and the annulus. In one or more embodiments, where a desirable pressure distribution is sought, an existing recipe for an annulus that results in an undesirable pressure distribution (e.g., the pressure distribution is outside of the desired pressure range or distribution range) is modified, a new annulus is formed from a new recipe, and pressure distribution between the formation sample and the new annulus is analyzed to determine whether the pressure distribution is within a tolerance of the desired pressure distribution. In some embodiments, the process illustrated in FIG. 2 is repeated until a new annulus recipe that forms an annulus having a desired pressure distribution is determined.

Figure 3:
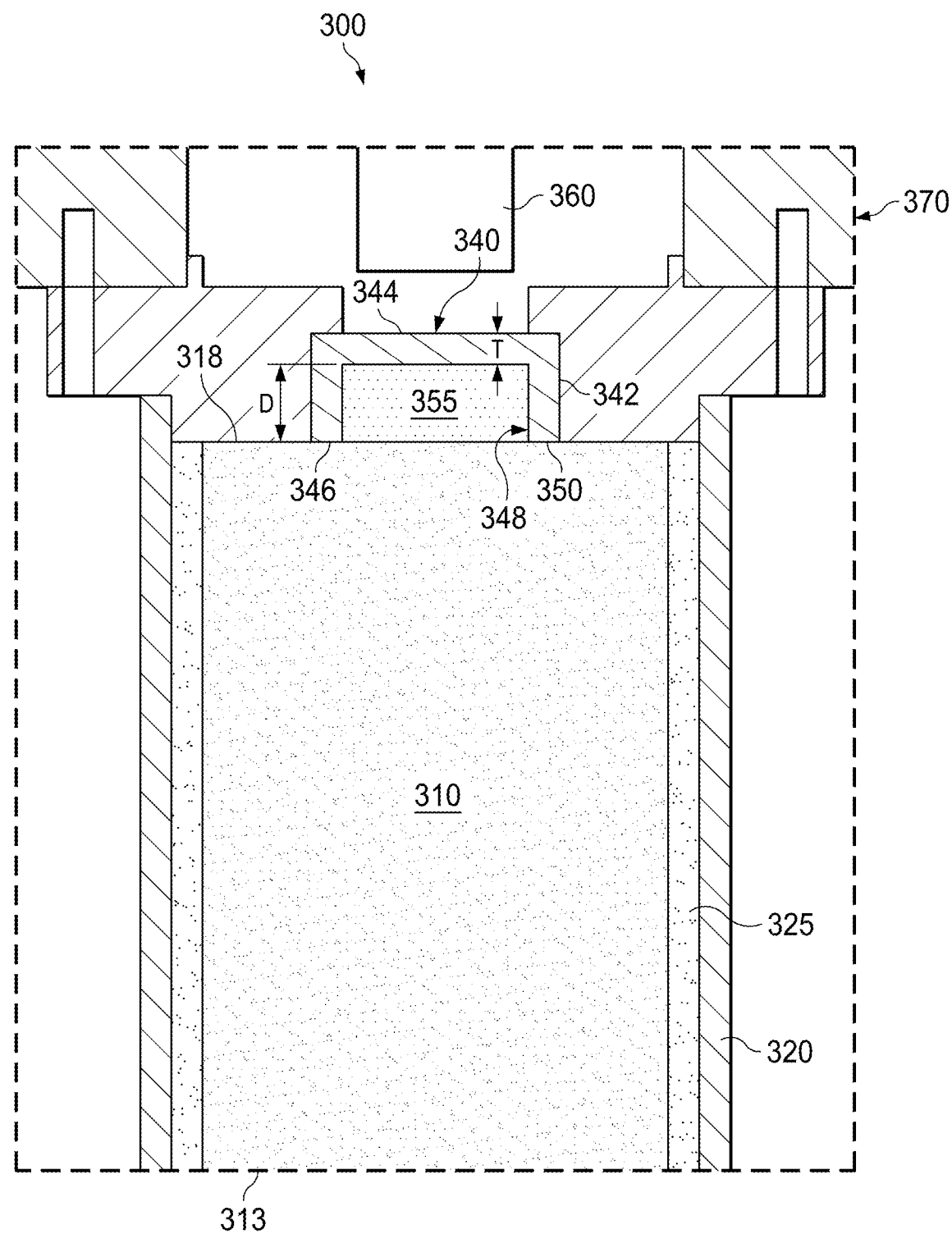
FIG. 3 illustrates a cross-sectional view of a test assembly of a pressure vessel used in the processes of FIGS. 1 and 2 and containing formation sample and samples of other materials used in subsequent well operations.

FIG. 3 illustrates a cross-sectional view of a test assembly 300 of a pressure vessel used in the processes 100 and 200 of FIGS. 1 and 2 and containing formation sample 310 and samples of other materials used in subsequent well operations.

The test assembly 300 includes the formation sample 310 having the pore axial end 313 and a wellbore facing end 318. The test assembly 300 further includes a sleeve 320 (e.g., an impermeable sleeve, bladder, etc.) surrounding a longitudinal circumference of the formation sample 310. The sleeve 320, in one embodiment, has an inner diameter a bit larger than the outer diameter of the formation sample 310, such that an annular space exists between the inner diameter of the sleeve 320 and the outer diameter of the formation sample 310. In one particular embodiment, the inner diameter of the sleeve 320 is about 1.25 cm larger than the outer diameter of the formation sample 310. Accordingly, wherein the formation sample 310 has a diameter of about 31.5 cm, the sleeve 320 might have an inner diameter of about 32.75 cm. Other embodiments exist, however, where no easily measurable space exists between the sleeve 320 and the formation sample 310, or wherein the dimensions are different than those disclosed.

In the particular embodiment of FIG. 3, a proppant 325 is placed within the annular space between the sleeve 320 and the formation sample 310. The proppant 325 may be a filler material that is spaced substantially equidistance around the formation sample 310. In at least one embodiment, rods are placed within the annular space such that the equidistance is created and the proppant 325 can then be placed therein. The proppant 325 may be uniform beads, such as ceramic, bauxite or any other suitable material.

The in-situ cement curing test fixture 340 in the illustrated embodiment is positioned over the wellbore facing end 318 of the formation sample 310. The in-situ cement curing test fixture 340, in accordance with the disclosure, includes a housing 342 having a first surface 344 and a second opposing surface 346. In accordance with one embodiment of the disclosure, an opening 348 exists within the housing 342, for example, extending only partially from the second opposing surface 346 to the first surface 344. In accordance with the embodiment of FIG. 3, the opening 348 defines a cup depth (D) and a cup base thickness (T). In accordance with one embodiment, the cup depth (D) simulates a desired downhole cement thickness and the cup base thickness (T) simulates a desired downhole wellbore casing thickness. Other in-situ cement curing test fixtures, different from that illustrated in FIG. 3, are within the scope of the disclosure.

The in-situ cement curing test fixture 340, in the illustrated embodiment, additionally includes a sealant 350 coupled to the second opposing surface 346 and entirely covering the opening 348. The sealant 350, when employed, maintains un-cured cement within the opening 348 as the un-cured cement is being cured in a rock flow core test system. In some embodiments, the sealant 350 is applied when the in-situ cement curing test fixture 340 is inverted as shown in FIG. 3 (e.g., prior to the un-cured cement fully curing), or when the second opposing surface 346 is below the first surface 344 (e.g., again prior to the un-cured cement fully curing).

The sealant 350, in one embodiment, is a gasket. When used, an adhesive material may be located on a circumference of the second opposing surface 346 to couple the gasket to the housing 342. In another embodiment, the sealant 350 is a more rigid structure that is coupled to the second opposing surface 346 using one or more fasteners (not shown). Notwithstanding the foregoing, the sealant 350 would desirably have little to no resistance to the firing of the perforation tool 360, and thus not significantly affect the testing of the formation sample 310.

Positioned within the opening 348, and in the embodiment of FIG. 3 held within the opening 348 by the sealant 350, is un-cured cement 355. The phrase un-cured cement, as that term is used herein, refers to cement that is still at least partially in fluid form, and thus remains flowable. The un-cured cement 355, in accordance with one embodiment, will be of the type most likely used in the wellbore of interest.

The test assembly 300 additionally includes the perforation tool 360 positioned proximate the first surface 344 of the in-situ cement curing test fixture 340. In the illustrated embodiment, the perforation tool 360 is positioned directly above the first surface 344. In another embodiment, however, the perforation tool 360 is positioned in direct contact with the first surface 344. The test assembly 300 additionally includes the wellbore test structure 370 at least partially surrounding the perforation tool 360 and the in-situ cement curing test fixture 340. The wellbore test structure 370 illustrated in FIG. 3 includes multiple adjoined pieces. In other embodiments, however, the wellbore test structure 370 includes a single piece.

Figure 4A:
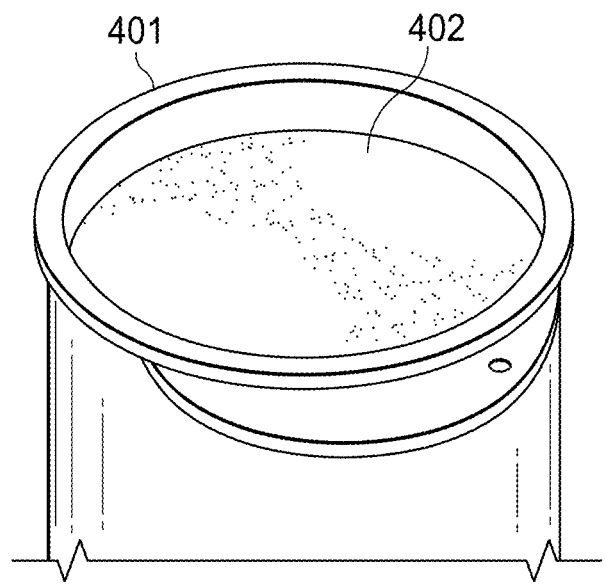
FIGS. 4A-4C illustrate a step-by-step process to deposit formation sample and pressure film into the test assembly of FIG. 3.
Figure 4B:
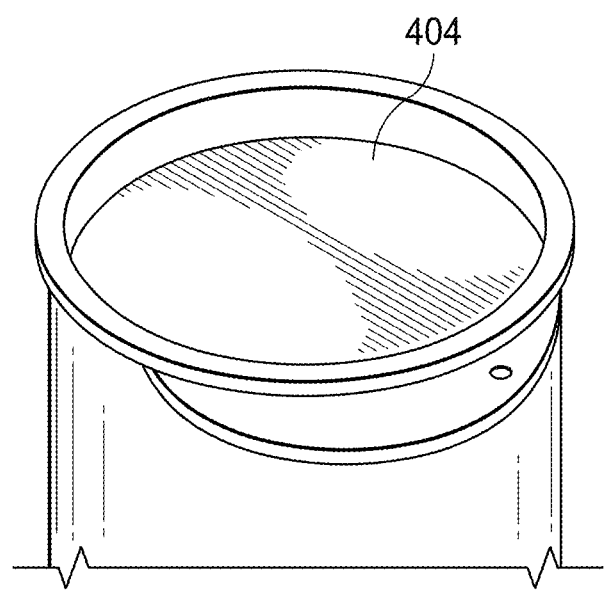
Figure 4C:
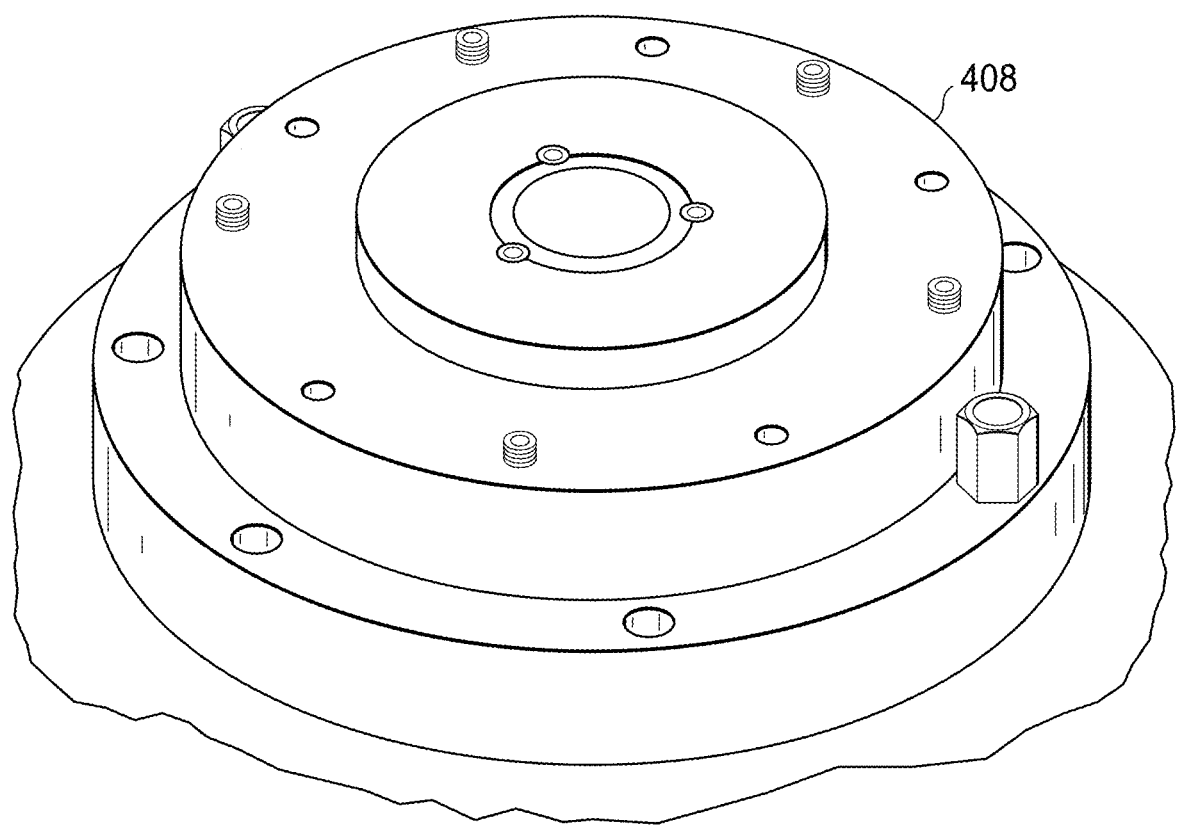

FIGS. 4A-4C illustrate a step-by-step process to deposit formation sample and pressure film illustrated into the test assembly 300 of the pressure vessel of FIG. 3. As shown in FIG. 4A, a formation sample 402 is deposited into a chamber 401 of test assembly 300 of FIG. 3. In FIG. 4B, pressure film 404 is overlaid on formation sample 402 of FIG. 4A. In some embodiments, where cement or another material is analyzed, the cement or material is overlaid on pressure film 404. In FIG. 4C, a lid 408 of the test assembly 300 of FIG. 3 is closed and one or more formation testing operations described herein are performed.

Figure 5:
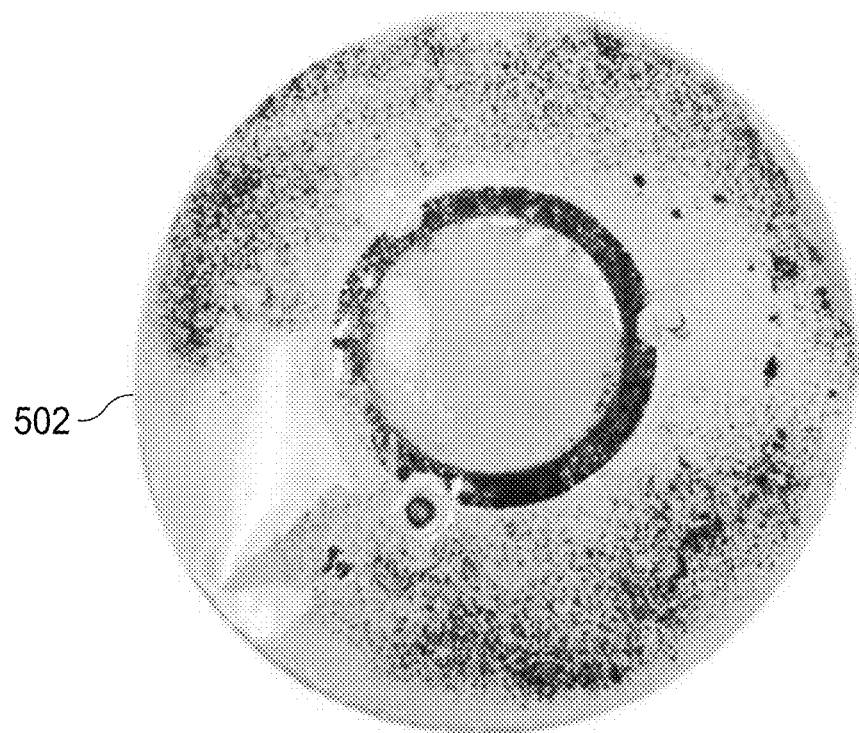
FIG. 5 illustrates a pressure film having a range of colors that illustrate the pressure distribution of the formation sample.

FIG. 5 illustrates a pressure film 502 having a range of colors that illustrate the pressure distribution of the formation sample. As illustrated in FIG. 5, a range of red colors (illustrated in FIG. 5 as different gradients of a greyscale) are present on pressure film 502 after testing operations described herein are performed on pressure film 502. The range of red colors correspond to the pressure distribution across areas of the formation sample that were placed under pressure film 502 during the testing operations. More particularly, the color at each location of interest of pressure film 502 corresponds to the amount of pressure experienced by the formation sample at a corresponding location of interest that is below the respective location of interest of the pressure film. In some embodiments, where pressure film 502 is placed between the formation sample and cement during a testing operation, the color distribution (e.g., range of red colors) on pressure film 502 corresponds to the pressure distribution between the cement and the formation sample during the testing operation. Similarly, where pressure film 502 is placed between the formation sample and an annulus during a testing operation, the color distribution (e.g., range of red colors) on pressure film 502 corresponds to the pressure distribution between the annulus and the formation sample during the testing operation.

The above-disclosed embodiments have been presented for purposes of illustration and to enable one of ordinary skill in the art to practice the disclosure, but the disclosure is not intended to be exhaustive or limited to the forms disclosed. Many insubstantial modifications and variations will be apparent to those of ordinary skill in the art without departing from the scope and spirit of the disclosure. For instance, although the flowcharts depict a serial process, some of the steps/processes may be performed in parallel or out of sequence, or combined into a single step/process. The scope of the claims is intended to broadly cover the disclosed embodiments and any such modification. Further, the following clauses represent additional embodiments of the disclosure and should be considered within the scope of the disclosure.

Clause 1, a method to determine pressure distribution along a downhole formation, the method comprising overlaying a pressure film on a formation sample of a downhole formation; inserting cement, the pressure film, and the formation sample in a pressure vessel; utilizing the pressure vessel to perform one or more tests of the formation sample; and after performing the one or more tests, analyzing the pressure film to determine a pressure distribution along the formation sample.

Clause 2, the method of clause 1, wherein analyzing the pressure film to determine the pressure distribution along the formation sample comprises analyzing the pressure film to determine the pressure distribution along surfaces of the formation sample and the cement.

Clause 3, the method of clauses 1 or 2, further comprising: pouring an annulus into a casing cup; and inserting the annulus into the pressure vessel, wherein the annulus is poured over the pressure film before the cement is poured over the pressure film.

Clause 4, the method of clause 3, wherein analyzing the pressure film to determine the pressure distribution along the formation sample comprises analyzing the pressure film to determine the pressure distribution along surfaces of the formation sample and the annulus.

Clause 5, the method of any of clauses 1-4, wherein performing the one or more tests comprises pressurizing the pressure vessel to match one or more downhole conditions.

Clause 6, the method of claim 1, further comprising: after performing the one or more tests, determining a color of the pressure film at a location of interest, wherein the location of interest of the pressure film overlays a corresponding location of interest of the formation sample during the one or more tests; and determining the pressure distribution based on the color of the pressure film at the location of interest of the pressure film.

Clause 7, the method of clause 6, further comprising: overlaying a second pressure film on the formation sample; after performing the one or more tests, determining a color of the second pressure film at a second location of interest of the second pressure film, wherein the second location of interest overlays the corresponding location of interest of the formation sample during the one or more tests; and determining the pressure distribution based on the color of the second pressure film at the second location of interest of the second pressure film.

Clause 8, the method of clause 7, wherein a first gradient of colors is illustrated on the pressure film in response to a first range of pressures applied to the formation sample, and wherein a second gradient of colors is illustrated on the second pressure film in response to a second range of pressures applied to the formation sample.

Clause 9, the method of clause 8, wherein at least one value of the first range of pressures applied to the formation sample overlaps at least one value of the second range of pressures applied to the formation sample, and at least one value of the first range of pressures applied to the formation sample does not overlap at least one value of the second range of pressures applied to the formation sample Clause 10, the method of clause 8, wherein the values of the first range of pressures applied to the formation sample do not overlap the values of the second range of pressures applied to the formation sample.

Clause 11, the method of any of clauses 1-10, further comprising pouring the cement into a casing cup, wherein the cement is cured before the cement is inserted into the pressure vessel Clause 12, a method to determine a recipe for materials used in a wellbore, the method comprising: overlaying a pressure film on a formation sample of a downhole formation; inserting cement, the pressure film, and the formation sample in a pressure vessel; utilizing the pressure vessel to perform one or more tests of the formation sample; after performing the one or more tests, analyzing the pressure film to determine a pressure distribution along the formation sample; and determining a recipe for manufacturing at least one material deployed in the wellbore based on the pressure distribution along the formation sample.

Clause 13, the method of clause 12, wherein the at least one material comprises the cement, and wherein analyzing the pressure film comprises analyzing the pressure film to determine a pressure distribution between the formation sample and the cement poured over the pressure film, and wherein determining the recipe for manufacturing the at least one material comprises determining the recipe for cement poured into the wellbore based on the pressure distribution between the formation sample and the cement poured over the pressure film.

Clause 14, the method of clause 13, further comprising determining one or more material properties of the cement poured into the wellbore, and wherein determining the recipe for the cement poured into the wellbore comprises determining the recipe for the cement poured into the wellbore that forms cement having the one or more material properties.

Clause 15, the method of any of clauses 12-14, further comprising: pouring an annulus into a casing cup; and inserting the annulus into the pressure vessel, wherein the annulus is poured over the pressure film before the cement is poured over the pressure film.

Clause 16, the method of clause 15, wherein the at least one material comprises annulus poured into the casing cup, wherein analyzing the pressure film to determine the pressure distribution along the formation sample comprises analyzing the pressure film to determine the pressure distribution along surfaces of the formation sample and the annulus, and wherein determining the recipe for manufacturing the at least one material comprises determining the recipe for annulus poured into the wellbore based on the pressure distribution between the formation sample and the annulus poured over the pressure film.

Clause 17, the method of any of clauses 12-16, further comprising: after performing the one or more tests, determining a color of the pressure film at a location of interest of the pressure film, wherein the location of interest overlays a corresponding location of interest of the formation sample during the one or more tests; and determining the pressure distribution based on the color of the pressure film at the location of interest of the pressure film.

Clause 18, the method of clause 17, further comprising: overlaying a second pressure film on the formation sample; after performing the one or more tests, determining a color of the second pressure film at a second location of interest of the second pressure film, wherein the second location of interest overlays the corresponding location of interest of the formation sample during the one or more tests; and determining the pressure distribution based on the color of the second pressure film at the second location of interest of the second pressure film.

Clause 19, the method of clause 18, wherein a first gradient of colors is illustrated on the pressure film in response to a first range of pressures applied to the formation sample, and wherein a second gradient of colors is illustrated on the second pressure film in response to a second range of pressures applied to the formation sample.

Clause 20, the method of clause 19, wherein at least one value of the first range of pressures applied to the formation sample overlaps at least one value of the second range of pressures applied to the formation sample, and at least one value of the first range of pressures applied to the formation sample does not overlap at least one value of the second range of pressures applied to the formation sample.

Unless otherwise specified, any use of any form of the terms "connect," "engage," "couple," "attach," or any other term describing an interaction between elements in the foregoing disclosure is not meant to limit the interaction to direct interaction between the elements and may also include indirect interaction between the elements described. As used herein, the singular forms "a", "an," and "the" are intended to include the plural forms as well, unless the context clearly indicates otherwise. Unless otherwise indicated, as used throughout this document, "or" does not require mutual exclusivity. It will be further understood that the terms "comprise" and/or "comprising," when used in this specification and/or the claims, specify the presence of stated features, steps, operations, elements, and/or components, but do not preclude the presence or addition of one or more other features, steps, operations, elements, components, and/or groups thereof. In addition, the steps and components described in the above embodiments and figures are merely illustrative and do not imply that any particular step or component is a requirement of a claimed embodiment.

It should be apparent from the foregoing that embodiments of an invention having significant advantages have been provided. While the embodiments are shown in only a few forms, the embodiments are not limited but are susceptible to various changes and modifications without departing from the spirit thereof.

The invention claimed is:

1. A method to determine pressure distribution along a downhole formation, the method comprising:
    overlaying a pressure film on a formation sample of a downhole formation;
    inserting cement, the pressure film, and the formation sample in a pressure vessel;
    utilizing the pressure vessel to perform one or more tests of the formation sample; and
    after performing the one or more tests, analyzing the pressure film to determine a pressure distribution along the formation sample.

2. The method of claim 1, wherein analyzing the pressure film to determine the pressure distribution along the formation sample comprises analyzing the pressure film to determine the pressure distribution along surfaces of the formation sample and the cement.

3. The method of claim 1, further comprising:
    pouring an annulus into a casing cup; and
    inserting the annulus into the pressure vessel, wherein the annulus is poured over the pressure film before the cement is poured over the pressure film.

4. The method of claim 3, wherein analyzing the pressure film to determine the pressure distribution along the formation sample comprises analyzing the pressure film to determine the pressure distribution along surfaces of the formation sample and the annulus.

5. The method of claim 1, wherein performing the one or more tests comprises pressurizing the pressure vessel to match one or more downhole conditions.

6. The method of claim 1, further comprising:
    after performing the one or more tests, determining a color of the pressure film at a location of interest of the pressure film, wherein the location of interest overlays a corresponding location of interest of the formation sample during the one or more tests; and
    determining the pressure distribution based on the color of the pressure film at the location of interest of the pressure film.

7. The method of claim 6, further comprising:
    overlaying a second pressure film on the formation sample;
    after performing the one or more tests, determining a color of the second pressure film at a second location of interest of the second pressure film, wherein the second location of interest overlays the corresponding location of interest of the formation sample during the one or more tests; and
    determining the pressure distribution based on the color of the second pressure film at the second location of interest of the second pressure film.

8. The method of claim 7, wherein a first gradient of colors is illustrated on the pressure film in response to a first range of pressures applied to the formation sample, and wherein a second gradient of colors is illustrated on the second pressure film in response to a second range of pressures applied to the formation sample.

9. The method of claim 8, wherein at least one value of the first range of pressures applied to the formation sample overlaps at least one value of the second range of pressures applied to the formation sample, and at least one value of the first range of pressures applied to the formation sample does not overlap at least one value of the second range of pressures applied to the formation sample.

10. The method of claim 8, wherein values of the first range of pressures applied to the formation sample do not overlap values of the second range of pressures applied to the formation sample.

11. The method of claim 1, further comprising pouring the cement into a casing cup, wherein the cement is cured before the cement is inserted into the pressure vessel.

12. A method to determine a recipe for materials used in a wellbore, the method comprising:
    overlaying a pressure film on a formation sample of a downhole formation;
    inserting cement, the pressure film, and the formation sample in a pressure vessel;
    utilizing the pressure vessel to perform one or more tests of the formation sample;

after performing the one or more tests, analyzing the pressure film to determine a pressure distribution along the formation sample; and determining a recipe for manufacturing at least one material deployed in the wellbore based on the pressure distribution along the formation sample.

13. The method of claim 12, wherein the at least one material comprises the cement, and wherein analyzing the pressure film comprises analyzing the pressure film to determine a pressure distribution between the formation sample and the cement poured over the pressure film, and wherein determining the recipe for manufacturing the at least one material comprises determining the recipe for cement poured into the wellbore based on the pressure distribution between the formation sample and the cement poured over the pressure film.

14. The method of claim 13, further comprising determining one or more material properties of the cement poured into the wellbore, and wherein determining the recipe for the cement poured into the wellbore comprises determining the recipe for the cement poured into the wellbore that forms cement having the one or more material properties.

15. The method of claim 12, further comprising:
pouring an annulus into a casing cup; and
inserting the annulus into the pressure vessel, wherein the annulus is poured over the pressure film before the cement is poured over the pressure film.

16. The method of claim 15, wherein the at least one material comprises the annulus poured into the casing cup, wherein analyzing the pressure film to determine the pressure distribution along the formation sample comprises analyzing the pressure film to determine the pressure distribution along surfaces of the formation sample and the annulus, and wherein determining the recipe for manufacturing the at least one material comprises determining the recipe for annulus poured into the wellbore based on the pressure distribution between the formation sample and the annulus poured over the pressure film.

17. The method of claim 12, further comprising:
after performing the one or more tests, determining a color of the pressure film at a location of interest of the pressure film, wherein the location of interest overlays a corresponding location of interest of the formation sample during the one or more tests; and
determining the pressure distribution based on the color of the pressure film at the location of interest of the pressure film.

18. The method of claim 17, further comprising:
overlaying a second pressure film on the formation sample;
after performing the one or more tests, determining a color of the second pressure film at a second location of interest of the pressure film, wherein the second location of interest overlays the corresponding location of interest of the formation sample during the one or more tests; and
determining the pressure distribution based on the color of the second pressure film at the second location of interest of the second pressure film.

19. The method of claim 18, wherein a first gradient of colors is illustrated on the pressure film in response to a first range of pressures applied to the formation sample, and wherein a second gradient of colors is illustrated on the second pressure film in response to a second range of pressures applied to the formation sample.

20. The method of claim 19, wherein at least one value of the first range of pressures applied to the formation sample overlaps at least one value of the second range of pressures applied to the formation sample, and at least one value of the first range of pressures applied to the formation sample does not overlap at least one value of the second range of pressures applied to the formation sample.

* * * * *